United States Patent [19]

Giani et al.

[11] Patent Number: 5,501,966
[45] Date of Patent: Mar. 26, 1996

[54] PSEUDOMONAS AERUGINOSA AND ITS USE IN A PROCESS FOR THE BIOTECHNOLOGICAL PREPARATION OF L-RHAMNOSE

[75] Inventors: Carlo Giani, Frankfurt am Main; Dieter Wullbrandt, Hofheim/Taunus; Reinhardt Rothert, Niedernhausen; Johannes Meiwes, Idstein, all of Germany

[73] Assignee: Hoechst Aktiengesellschaft, Frankfurt am Main, Germany

[21] Appl. No.: 375,230

[22] Filed: Jan. 19, 1995

Related U.S. Application Data

[63] Continuation of Ser. No. 80,257, Jun. 23, 1993, abandoned.

[30] Foreign Application Priority Data

Jun. 25, 1992 [DE] Germany .......................... 42 20 437.2
Jul. 31, 1992 [DE] Germany .......................... 42 25 283.0

[51] Int. Cl.$^6$ ............................ C12P 19/02; C12P 19/44; C12N 1/20
[52] U.S. Cl. .................... 435/105; 435/74; 435/253.3
[58] Field of Search ................................. 435/74, 253.3, 435/105; 536/4.4

[56] References Cited

U.S. PATENT DOCUMENTS

| | | | |
|---|---|---|---|
| 4,628,030 | 12/1986 | Kaeppeli et al. | 435/101 |
| 4,814,272 | 3/1989 | Wagner et al. | 435/74 |
| 4,933,281 | 6/1990 | Daniels et al. | 435/101 |
| 5,077,206 | 12/1991 | Cheetham et al. | 435/99 |

FOREIGN PATENT DOCUMENTS

| | | |
|---|---|---|
| 0317033 | 5/1989 | European Pat. Off. . |
| 2150375 | 4/1972 | Germany . |
| 62-293 | 1/1987 | Japan . |
| 2194247 | 3/1988 | United Kingdom . |

OTHER PUBLICATIONS

Shabtai, Y.; Applied Environmental Microbiology; 57(6): 1740–45 (1991); "Isolation and Characterization of a Lipolytic Bacterium Capable of . . . ".
Biotechnology and Bioengineering, vol. 33, pp. 365–368 (1989) "Microbially Produced Rhamnolipid as a Source . . . ", R. J. Lindhardt et al.
Enzyme Microb. Technol., vol. 10, pp. 198–206 (1988), "Microbial Polysaccharides Containing 6–deoxysugars," Marianne Graber et al.
J. Amer. Chem. Soc. vol. 71, pp. 4124–4126 (1945), "A Glyco–lipide Produced by *Pseudomonas aeruginosa*," F. G. Jarvis et al.
J. Bacteriol, vol. 68, pp. 645–654 (1954), "Studies on the Production of Glycolipide by *Pseudomonas aeruginosa*," George Hauser et al.
Commission of the European Communities, ECLAIR Program, Contract No. AGRE–0011–C, Report No. 2, "Microbial Production of a Precursor . . . ".
Microbiological Sciences, vol. 3, No. 5, (1986), pp. 145–149, "Biosurfactants," D. G. Cooper.
Surfactant Science Series, vol. 25, (1987), pp. 89–120, "Production of Biosurfactants," Christoph Syldatk et al.
Agricultural Biological Chem., vol. 35, No. 5, pp. 868–692 (1971), "Formation of Rhamnolipid by *Pseudomonas aeruginosa* . . . ," Hisatsuka et al.
Applied and Enviromental Microbiology, vol. 51, No. 5, pp. 985–989 (1986), "Pilot Plant Production of Rhamnolipid . . . ," H. E. Reiling et al.
J. Chem. Tech. Biotechnol., vol. 45, pp. 249–257 (1989), "Factors Affecting Biosurfactant Production Using . . . ," K. Venkata Ramana et al.
Z. Naturforsch. 40c, pp. 61–67 (1985), "Production of Four Interfacial Active Rhamnolipids from n–Alkanes or Glycerol . . . ," C. Syldatk et al.
Biochemimica et Biophysica Acta, vol. 1045, pp. 189–193 (1990), "Characterisation of *Pseudomonas rhamnolipids*," Nigel B. Rendell et al.
G. Thieme Verlag Stuttgart, 6th Edition, pp. 182–186 (1985), "Allgemeine Mikrobiologie" (General Microbiology), Hans G. Schlegel.
Guerra–Santos et al, Appl. Microbiol. Biotechnol., 24:443–448 (1986).

*Primary Examiner*—John W. Rollins
*Assistant Examiner*—Francisco Co. Prats
*Attorney, Agent, or Firm*—Finnegan, Henderson, Farabow, Garrett & Dunner

[57] ABSTRACT

*Pseudomonas aeruginosa* and its use in a process for the biotechnological production of L-rhamnose
Bacterial strains are capable of the formation of rhamnolipids, which they generate in the culture solution. If bacteria of the type *Pseudomonas aeruginosa* are employed for the fermentation, these microorganisms synthesize rhamnolipids in a concentration of 70–120 g/l of culture solution. The L-rhamnose can be recovered directly from the culture solution by hydrolysis of the rhamnolipids, i.e. without a complicated separation of the cell material and without isolation of the rhamnolipids before hydrolysis.

8 Claims, No Drawings

PSEUDOMONAS AERUGINOSA AND ITS USE IN A PROCESS FOR THE BIOTECHNOLOGICAL PREPARATION OF L-RHAMNOSE

This application is a continuation of application Ser. No. 08/080,257 filed Jun. 23, 1993, now abandoned.

The deoxysugar L-rhamnose (6-deoxy-L-mannose) is very highly suitable as a chiral component for the preparation of various organic compounds. L-Rhamnose or its derivatives find wider and wider use in the synthesis of pharmaceutical products and plant protection agents, as well as in the field of cytology of plant and animal cells, microbiology, immunobiology and aroma production. For example, using L-rhamnose as the starting compound, 2,5-dimethyl-4-hydroxy-2,3-dihydrofuran-3-one(Furaneol®) can be prepared, which is used in turn as a constituent of various aromatic substances in the foodstuffs and perfume industry.

The sugar L-rhamnose is only accessible with great difficulty via chemical routes. However, it can be obtained from various natural sources by extraction after acidic or enzymatic hydrolysis, for example from the flavonoid glycosides hesperidine, rutine, naringine, quercitrin or for example from gum arabic or sea algae [Biotechnology and Bioengineering, Vol. 33, p. 365 (1989), R. J. Linhardt et al.; EP-A-0 317 033; JPA 62293; U.S. Pat. No. 5,077,206, Cheetham et al.]. The process-intensive isolation steps for L-rhamnose, partly using organic solvents, also the aromatic, potentially toxic waste products obtained in the work-up and the constituents of the natural sources, which vary in composition and are dependent on the seasonal rhythm, turn out to be disadvantageous for the acidic hydrolysis processes.

U.S. Pat. No. 5,077,206 claims a process for the preparation of L-rhamnose from plant material using several enzymes and subsequently several purification steps. A disadvantage of this process is the difficult separation of the L-rhamnose from the sugars originating from the plant material, in particular from glucose, on account of the strong chemical structural similarities of the sugars (also including the molecular weight).

L-Rhamnose can also be produced by fermentation in the form of rhamnose-containing heterpolysaccharides with the aid of bacteria of various orders such as, e.g. Alcaligenes, Acinetobacter, Klebsiella, Streptococcus or Lactobacillus. [Enzyme Microb. Technol., Vol. 10, p. 198 (1988), M. Graber et al.; J. Amer. Chem. Soc., Vol. 71, p. 4124 (1945), F. G. Jarvis and M. J. Johnson; J. Bacteriol., Vol. 68, p. 645 (1954), G. Hauser and M. L. Karnovsky].

Disadvantages of this process are the usually viscosity-related low yields and the difficult separation of the L-rhamnose (reasons: see above) from a mixture of various sugars required after hydrolytic cleavage of the heteropolysaccharide. In a further literature reference, a rhamnose-containing heteropolysaccharide is described which is prepared by fermentation using a bacterium of the order Klebsiella. The rhamnose yields are about 17 g/l, relative to the culture solution [Commission of the European Communities, ECLAIR Program, Contract No. AGRE-0011-C, Report No. 2 (final report) 1991].

A further biogenic source of 6-deoxysugars are the glycolipids, which can be prepared by fermentation [Microbiological Sciences Vol. 3, No. 5, p. 145, (1986), D. G. Cooper; Surfactant Sci. Series, Vol. 25, p. 89 (1987), Christoph Syldatk and Fritz Wagner; Biotechnology and Bioengineering, Vol. 33, p. 365 (1989), R. J. Linhardt et al.; U.S. Pat. No. 4,933,281, Daniels et al.; U.S. Pat. 4,814,272, Wagner et al.].

It has been known for a long time that rhamnolipids are formed from the bacterium *Pseudomonas aeruginosa* [J. Amer. Chem. Soc., Vol. 71, p. 4124 (1949), F. G. Jarvis et al.; J. Bacteriol., Vol. 68, p. 645 (1954) George Hauser and Manfred L. Karnovsky]. Numerous publications and patents are concerned with the production of rhamnolipids by *Pseudomonas aeruginosa* by means of fermentation. [Applied and Environmental Microbiology, Vol. 51, No. 5, p. 985 (1986), H. E. Reiling et al.; J. Chem. Techn. Biotechnol., Vol. 45, p. 249 (1989), K. Venkata Ramana et al.; U.S. Pat. No. 4 933 281, Daniels et al.; Deutsche Offenlegungsschrift 2 150 375, 1972; U.S. Pat. No. 4 814 272, Wagner et al.]

In the culture solution of *Pseudomonas aeruginosa*, mainly 4 rhamnolipids (RL1–RL4,) are present, which consist of 1 or 2 L(+)-rhamnose units and one or two β-hydroxydecanoic acids [Z. Naturforsch. 40 c, p. 61 (1985), C. Syldatk et al. ].

Rhamnolipids from Pseudomonas aeruginosa

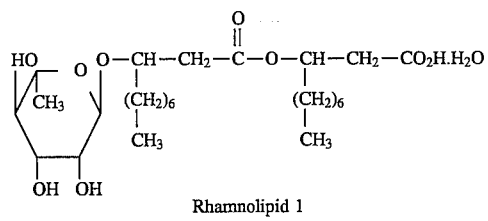

Rhamnolipid 1

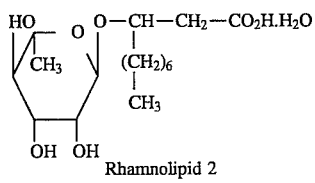

Rhamnolipid 2

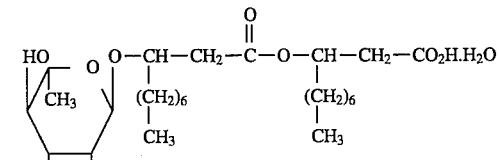

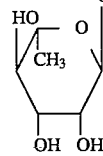

Rhamnolipid 3

-continued
Rhamnolipids from Pseudomonas aeruginosa

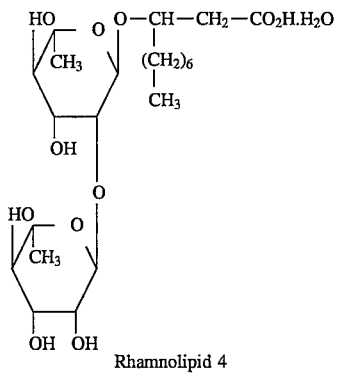

Rhamnolipid 4

A new publication shows that *Pseudomonas aeruginosa* is able to form other rhamnolipids [Biochimica et Biophysica Acta, Vol. 1045, p. 189, (1990) N.B. Rendell et al.]. According to amount, however, these cannot compete with the rhamnolipids 1–4. They are composed, besides L-rhamnose and β-hydroxydecanoic acid, additionally of 3-hydroxyoctanoic acid, 3-hydroxydodecanoic acid or 3-hydroxydodec-5-enoic acid.

Besides glucose, glycerol, n-alkanes, fatty alcohols and fatty acids, vegetable oils such as soybean oil or olive oil are also suitable as carbon sources for rhamnolipid production [Z. Naturforsch. 40 c, p. 61 (1985), C. Syldatk et al.; Surfactant Sci. Series, Vol. 25, p. 89 (1987), C. Syldatk et al.; Applied and Environmental Microbiology, Vol. 51, No. 5, p. 985 (1986), H. E. Reiling et al.; Biotechnology and Bioengineering, Vol. 33, p. 365 (1989), R. J. Linhardt et al.; Agr. Biol. Chem. Vol. 35, No. 5, p. 686 (1971), H. Hisatsuka et al.; U.S. Pat. 4,814,272, Wagner et al.].

The ratio of the rhamnolipids to one another and their yields depend essentially on the culture conditions [Z. Naturforsch. 40 c, p. 61 (1985), C. Syldatk et al.; Tenside Surf. Det. 27, 5, p. 302 (1990), J. L. Parra et al.].

Thus, Parra et al. showed that mainly RL1 and RL3 are formed when using olive oil as a carbon source.

The maximum yields of rhamnolipids achieved until now by fermentation are described in U.S. Pat. No. 4 933 281 (Daniels et al.). From the claims, it follows that when using corn oil as a carbon source, after the fermentation of a *Pseudomonas aeruginosa* strain the rhamnolipids can be isolated from the culture medium in a concentration of 30–50 g/l. Isolation is carried out in order to obtain purified rhamnolipids. In the subsequent hydrolysis of the isolated rhamnolipids, L-rhamnose and hydroxydecanoic acid are formed as reaction products.

The examples contained in the patent, in particular Example 3, make it clear that the rhamnolipid concentration of 30–50 g/l given in the claims is related to the concentrations present in the culture solution.

A process for the preparation of L-rhamnose by fermentation of *Pseudomonas aeruginosa* has now surprisingly been found, with the aid of which rhamnolipid concentrations of 70–120 g/l are achieved in the fermentation solution. The preparation of the L-rhamnose is carried out without a complicated separation of the cell mass from the culture solution and without an isolation of the rhamnolipids before the hydrolysis.

The invention thus relates to:

1. *Pseudomonas aeruginosa* which synthesizes rhamnolipids in a concentration of from 70–120 g/l of culture solution.

A process for the preparation of L-Rhamnose, which comprises synthesizing rhamnolipids in a concentration of from 70–120 g/l of culture solution by fermentation of *Pseudomonas aeruginosa* and hydrolyzing the rhamnolipids to L-rhamnose.

The invention is described in detail in the following. It is also defined by the contents of the claims.

The fermentation can be carried out on the laboratory scale (fermentation amount in the liter range) as well as on the industrial scale (e.g. on the 20–50 $m^3$ scale).

Percentage data, unless stated otherwise, relate to the weight.

As microorganisms, all strains of bacteria can be fermented which secrete rhamnolipids into the culture supernatant.

The microorganisms are isolated from their natural environment with the aid of enrichment cultures. This procedure is known to the person skilled in the art. In brief:

The enrichment conditions are those under which an organism competes successfully. For oil- and fat-loving microorganisms, such as, e.g. *Pseudomonas aeruginosa*, minimal media containing oils, fats and/or hydrocarbons are used as carbon sources. These environmental conditions are prepared and inoculation is carried out with a mixed population, as is present in the natural environment. In an enrichment nutrient solution of this type, the desired bacterial strains are successful and overgrow all accompanying organisms. The enriched strain can be easily isolated by transferring to the same nutrient solution several times and distributing on a solid nutrient medium. A frequent "liquid-liquid inoculation", which is carried out after short intervals, prevents the growth of accompanying organisms which would utilize the excretion or even autolysis products of the primarily favored cells (Allg. Mikrobiologie (General Microbiology) by H. G. Schlegel, 6th Edition, p. 182, G. Thieme Verlag Stuttgart, New York).

Bacteria are preferably used which have been isolated from an enrichment culture of a water sample. In particular, the water sample of an oil- and fat-processing operation is used.

The water sample used originates from the works' own water. The strain isolated from this water sample was classified as *Pseudomonas aeruginosa* by the German Collection of Microorganisms and Cell Cultures GmbH, Mascheroder Weg 1 B, W-3300 Brunswick, Germany.

The cells of *Pseudomonas aeruginosa* are rod-shaped, have a diameter of about 0.6–0.8 μm, are about 1.5–3.0 μm long and are mobile.

After isolation, mutagenization of *Pseudomonas aeruginosa* is carried out. *Pseudomonas aeruginosa* is mutagenized in a manner known per se with the aid of the chemical mutagen N-methyl-N'-nitro-N-nitrosoguanidine (MNNG).

After mutagenesis of *Pseudomonas aeruginosa*, cell isolation to isolate producer strains is carried out with the aid of flow cytometry. In this process, the optical properties of the suspended, MNNG-treated cells were measured in flow. Cells of typical or different size and shape were thus automatically isolated in different nutrient media.

A commercially available cytofluometer with the following equipment is used: argon laser (wavelength: 488 m, power: 20 mW); measuring device for the optical signals forward scattered light and 90° scattered light to assess the cell size and shape; automatic sorting unit.

The sorting of individual cells was carried out on 2 different nutrient media, a glycerol minimal nutrient medium and a soybean oil minimal nutrient medium, known to the person skilled in the art.

After incubation of the nutrient medium at 37° C., the individual cells grown to give clones were tested in shaker flasks and small fermenters for their rhamnolipid productivity.

In this way, it was possible to isolate 2 high-efficiency mutants of *Pseudomonas aeruginosa*. These mutants are particularly preferably employed for the fermentation and thus for the preparation of L-rhamnose.

They are rod-shaped, just like the non-mutagenized *Pseudomonas aeruginosa*, have a diameter of about 0.6–0.8 μm, are about 1.5–3.0 μm long and are mobile.

The high-efficiency mutants of *Pseudomonas aeruginosa* were deposited under the names DSM 7107 and DSM 7108 in the German Collection of Microorganisms and Cell Cultures GmbH, Mascheroder Weg 1 B, W-3300 Brunswick, Germany, on the 16th Jun. 1992 according to the rules of the Budapest Treaty.

Mutants of this type can also be produced in other known ways by physical means, for example irradiation with ultraviolet rays or X-rays or with the aid of other chemical mutagens, such as, for example, ethyl methanesulfonate (EMS) or 2-hydroxy-4-methoxybenzophenone (MOB).

The procedure described in the following applies to all *Pseudomonas aeruginosa* isolates.

*Pseudomonas aeruginosa* is fermented in a medium containing vegetable oils as the carbon source. Examples of vegetable oils are rape, olive, corn and sunflower oil. Apart from vegetable oil, the medium must additionally contain one or more nitrogen sources, sulfate and magnesium ions and potassium and chloride ions, one or more phosphorus sources and trace elements. The vegetable oil particularly used is soybean oil in concentrations of about 100–250 g/l of nutrient solution, where concentrations between 125 g/l and 165 g/l are to be preferred.

Nitrogen sources which can be used are nitrogen sources known to the person skilled in the art, such as e.g. $(NH_4)_2SO_4$ in concentrations of from 5–50 g/l of nutrient solution, $NaNO_3$ in a concentration of 15 g/l being preferably employed.

To make available sulfate and magnesium ions, 0.01–2 g/l of $MgSO_4 7H_2O$, preferably 0.5 g/l are employed. The potassium and chloride ions required for production can be made available by the use of 0.1 to 5 g/l of KCl, where 1 g/l is preferred.

A 0.001 to 0.1 molar sodium phosphate buffer is employed as a phosphorus source and for buffering the medium. Preferably, about 6.5 g/l of a 75% strength phosphoric acid and about 8.9 g/l of a 33% strength sodium hydroxide solution are used for this purpose.

An $FeCl_3$-containing trace element solution containing various metal salts, dissolved in an aqueous solution of sodium citrate, is added in a 4- to 5-fold concentration after the sterilization of the medium or is preferably added to the fermentation solution 4–5 times in the initial concentration at different times.

The pH of the nutrient solution should be between pH 5.5 and 7.5 at the start of fermentation, preferably around pH 6.3 and does not need to be controlled in the course of the fermentation.

Aeration is carried out using sterile air, which is blown into the stirred fermentation solution. The aeration rates vary between 0.02 and 0.5 VVM (Volume of Air per Volume of Fermentation Solution per Minute) and are dependent on the fermenter geometry, the stirrer geometry, the energy input, but in particular on the current state of the fermentation solution. Typically, about 0.3±0.05 VVM are set in the growth phase and 0.1±0.03 VVM in the production phase.

Depending on the foaming behavior of the fermentation solution, about 5–15 ml/l culture solution of a commercially available silicone antifoam agent are added during the fermentation, for example Silicone Antifoam Agent VP 1133 from Wacker Chemie GmbH (Munich, Germany).

The fermentation temperature is between 20° C. and 40° C., preferably around 30°–35° C. The fermentation period is about 4–11 days, preferably 6–8 days. The Pseudomonas aeruginosa strains can be fermented as individual or mixed cultures. DSM 7107 and 7108 are both very highly suitable for fermentation on the laboratory scale and on the industrial scale.

Under the abovementioned fermentation conditions, the microorganisms form mainly the rhamnolipids 1 and 3 (FIG. 1) with a volumetric overall productivity of rhamnolipids of about 70–120 g/l of culture solution. Concentrations of L-rhamnose of 30–50 g/l are achieved here.

The recovery of the L-rhamnose is carried out by direct hydrolysis of the rhamnolipids, i.e. without separation of the cell material and without isolation of the rhamnolipids before their hydrolysis to L-rhamnose.

Apart from the rhamnolipids, still undigested vegetable oil, mainly soybean oil, dead cells, all the culture medium constituents not consumed by the microorganisms, fatty acids, antifoams, dissolved salts and other bacterial metabolic products not specified in greater detail are found in the culture solution.

For further work-up of the fermentation solution, the bacteria contained in it are first killed by heating the complete fermenter contents to 80°–120° C., preferably to 100° C. and maintaining this temperature for 15–90 min, preferably 60 min.

The further process steps of the work-up of the cooled culture broth, which is essentially an aqueous emulsion, are described in the Offenlegungsschrift PCT-EP 91-01756 ("Process for the preparation of purified glycolipids by membrane separation processes") and the Offenlegungsschrift PCT-EP 91-01426 ("Process for the preparation of L-rhamnose from rhamnolipids").

The work-up steps for the isolation of the rhamnose in logical sequence are:

1. Acidification of the heat-inactivated culture solution.
2. Concentration by ultrafiltration on membranes having a separation limit of 30,000 to 300,000 daltons.
3. Desalting by diafiltration on the same membrane.
4. Hydrolysis of the desalted concentrate at a pH of 0–3 and a temperature of 120°–150° C.
5. Separation of the aqueous, rhamnose-containing phase from the lipid phase.
6. Purification of the aqueous phase at pH 3–8 by treatment with decolorizing agents such as activated carbon or bentonite or by ion exchange chromatography.
8. Crystallization of the L-rhamnose from the concentrated aqueous phase.

The acidification of the heat-inactivated culture solution is carried out with acids, in particular either with $H_2SO_4$, if the continuous hydrolysis of the rhamnolipids is carried out to give L-rhamnose or in the case of "batch hydrolysis", in particular with HCl or $H_2SO_4$.

Under these acidic conditions, glycolipids which could normally pass through the ultrafiltration membrane are retained.

Following the ultrafiltration, the salts are partially washed out by means of diafiltration on the same membrane by permanent addition of water and removal of filtrate. The salt concentration is determined during the filtration by conductivity measurements. Conductivity measurement is carried out using commercially available electrodes.

As a result of this procedure (concentration and washing), an aqueous, 2-3 times concentrated solution is formed, which essentially comprises the following constituents: non-metabolized fatty acids and soybean oil residues, salts (conductivity reduced to about 20%), dead cells, antifoams, rhamnolipids and other bacterial, relatively high molecular weight metabolic products. The rhamnolipids are completely retained in this procedure.

The chemical hydrolysis of the rhamnolipids is carried out without prior isolation directly in the culture solution which has been treated as described above.

The chemical hydrolysis takes place in the homogenized state, i.e. with stirring. Following the hydrolysis, the aqueous and lipid-containing phases are separated by methods known to the person skilled in the art. The L-rhamnose is isolated from the aqueous phase.

If $H_2SO_4$ was employed in the first step (acidification step), the aqueous phase is treated with $Ca(OH)_2$ or $CaCO_3$ to remove $H_2SO_4$. The aqueous phase is finally purified at pH 3–8 by treatment with decolorizing agents or by ion exchange chromatography. The hydroxydecanoic acid formed during the hydrolysis in small amounts is not isolated.

3. Examples 3.1. Example 1:

Production of the *Pseudomonas aeruginosa* isolates:

a) Enrichment culture

The microorganisms are obtained from the works' own water samples. To do this, about 10 ml of waste water sample are incubated at 37° C. for 3 days on a shaker in a 500 ml Erlenmeyer flask containing 200 ml of enrichment medium (mineral salt medium see below).

Mineral salt medium:

15 g/l of olive oil 10 g/l of $NANO_3$ 0.1 g/l of $CaCl_2 \cdot 2H_2O$ 0.4 g/l of $MgSO_4 7H_2O$ 6.8 g/l of $KH_2PO_4$ 8.7 g/l of $K_2HPO_4 \cdot 3H_2O$ 5 ml/l of trace salts Deionized water Trace salts:

1 g/l of iron(III) citrate 0.2 g/l of $MnSO_4$ 0.1 g/l of $ZnCl_2$ 0.025 g/l of $CuSO_4 \cdot 5H_2O$ 0.02 g/l of sodium tetraborate 0.01 g/l of sodium molybdate 0.004 g/l of $CoCl_2$ Deionized water 2 ml of the 1st enrichment culture are incubated again as described above in a 2nd flask containing the same medium. This process is repeated a further four times.

b) Isolation

The culture solution of the last enrichment culture is plated out onto an Agar plate containing complete medium comprising 10 g/l of glucose, 4 g/l of casein peptone, 4 g/l of meat extract, 0.5 g/l of yeast extract, 0.5 g/l of liver extract and 2.5 g/l of NaCl. After incubation at 37° C., *Pseudomonas aeruginosa* is isolated as a clone.

c) MNNG mutagenesis The clone from Example 1, paragraph b, is cultured in the complete medium at 37° C. for 24 hours. The culture medium is then diluted 1:10 with fresh complete medium. The cells are regenerated at 37° C. for 2 hours on the shaker.

The cells separated off by centrifugation, and washed in a tris-maleic acid buffer (pH 6) and taken up again are treated with MNNG (0.4–0.8 mg/ml) at 37° C. for 15–20 min on the shaker.

After repeated washing of the cells three times in trismaleic acid buffer, the mutagenized cell suspension is cultured in the complete medium at 37° C. for 24 hours. A cell isolation is then carried out with the aid of flow cytometry.

The sorting of the individual cells is carried out on the following nutrient medium:

Minimal nutrient medium:

20 g/l of glycerol (or soybean oil**)

10 g/l of $NaNO_3$ 1 g/l of KCl 1 g/l of NaCl 0.02 g/l of $CaC_2 \cdot 2H_2O$ 6.8 g/l of $KH_2PO_4$ 8.7 g/l of $K2HPO_4$ 0.5 g/l of $MgSO_4 \cdot 7H_2O$ 2 ml/l of trace element solution*

20 g/l of agar

Deionized water pH adjustment to pH 6.5 before sterilization

* Addition after sterilization

** Homogenization of the heated nutrient medium shortly before pouring

Trace element solution:

1 g/l of sodium citrate-$2H_2O$ 0.14 g/l of $FeCl_3 \cdot 6H_2O$ 0.7 g/l of $ZnSO_4 \cdot 7H_2O$ 0.6 g/l of $CoCl_2 \cdot 6H_2O$ 0.6 g/l of $CuSO_4 \cdot 5H_2O$ 0.4 g/l of $MnSO_4 \cdot 5H_2O$ Deionized water The strains obtained in this manner are employed for the fermentation described in the following.

3.2. Example 2:

Batch fermentation on the industrial scale for the production of L-rhamnose a) Preculture A first preculture of the strain Pseudomonas aeruginosa DSM 7107 in 4 l of preculture nutrient solution (Tab. 1) is prepared in shaker flasks (2 l Erlenmeyer flasks each containing 500 ml of nutrient solution, at 30° C., 200 rpm, 20 h). The complete 1st preculture is used for the inoculation of the 2nd preculture (350 l).

To do this, the strain DSM 7107 is fermented aerobically at an aeration rate of 180 l of air/min, a stirring speed of 300 rpm, and at a temperature of 28° C. for 16 hours in a 450 l fermenter containing 350 l of the complex preculture nutrient solution (Table 1).

Tab. 1: Preculture nutrient solution:

10 g/l of glucose 5 g/l of casein peptone 1 g/l of yeast extract 0.5 g/l of NaCl Water The complete 2nd preculture is used for the inoculation of the main culture.

b) Main culture 17 m³ of the nutrient solution given in Table 2 are prepared in a fermenter having about 30 m³ nominal volume:

Table 2: Main culture nutrient solution:

6.47 g/l of 75% strength $H_3PO_4$ about 8.94 g/l of 33% strength NaOH 0.5 g/l $MgSO_4 \cdot 7H_2O$ 1 g/l KCl 15 g/l $NaNO_3$ 125 g/l soybean oil Water To do this, after introduction of the required amount of water a pH of 6.8 is established using $H_3PO_4$ and NaOH. After addition of the residual nutrient solution constituents, the pH is corrected to pH 6.2 using $H_2SO_4$.

After sterilization for 45 minutes, a pH of about 6.3 is established. In a separate container, a solution containing trace elements (Tab. 3) is sterilized. To do this, the following substances are dissolved in 150 l of deionized water and sterilized:

Tab. 3: Trace elements solution:

2 mg/l of sodium citrate·$2H_2O$ 0.28 mg/l $FeCl_3 \cdot 6H_2O$ 1.4 mg/l $ZnSO_4 \cdot 7H_2O$ 1.2 mg/l $CoCl_2 \cdot 6H_2O$ 1.2 mg/l $CuSo_4 \cdot 5H_2O$ 0.8 mg/l $MnSo_4 \cdot 1H_2O$ Deionized water Concentration data relate to 1 l of main culture This trace element solution is added to the main fermenter under sterile conditions before inoculation and 3 times further after fermentation periods of about 20, 40 and 70 hours.

The complete contents of the prefermenter (350 l) are used as the inoculum. The fermentation temperature is 30° C. In the first 10 hours of fermentation, aeration is carried out using 250 m³ of air/hour, from the 10th to the 30th hour using 400 m³/h and from the 30th hour using 100–75 m³/h.

For foam control, a separately sterilized silicone antifoam agent VP 1133 (Wacker) is used which, depending on the foaming behavior of the fermentation solution, is metered into the fermenter in portions utilizing a foam electrode.

The stirring component employed is a radial stirrer having four turbines, which have a diameter of 1040 mm (stirrer φ: fermenter φ=0.4:1). The speed of rotation in the first 10 hours of fermentation is 50 rpm, and 75 rpm from the 10th hour.

Under the abovementioned fermentation conditions, about 78 g of rhamnolipids and an L-rhamnose content of about 32 g of L-rhamnose can be produced per liter of culture solution in a fermentation period of 167 hours. After fermentation is complete, the complete fermentation solution is heated to 100° C. in the fermenter and stirred at this temperature for 1 hour to kill the production strain. Further working-up steps as far as crystalline L-rhamnose are carried out analogously to the patents PCT/EP 91-01756 and PCT/EP 91-01426.

3.3 Example 3:

Fed-batch fermentation on the industrial scale for the production of L-rhamnose 18.5 m³ of main culture medium having the composition from Example 1 are inoculated with 350 l of preculture (also described in Example 1). The production strain employed is the strain *Pseudomonas aeruginosa* DSM 7108. Before inoculation and after fermentation periods of 20, 40, 70 and 120 hours, a trace element solution (see Example 1) is added under sterile conditions in each case.

The aeration rates are varied as follows: At the start of fermentation 250 m³/h, after 10 hours of fermentation 350 m³/h and after 30 hours of fermentation, depending on the intensity of foam formation, 100–130 m³/h of air.

In the first 10 hours of fermentation, the mixture is stirred at 50 rpm, then at 75 rpm. From the 72nd to the 109th hours of fermentation, a further 564 l of soybean oil are continuously metered in.

Foam control is carried out in the same manner as was described in Example 1. Under said fermentation conditions, 95 g/l of rhamnolipids and a content of L-rhamnose of 39–40 g/l are produced in the culture solution in 9 days. Further working up of the culture solution is carried out as was described in Example 1.

3.4 Example 4:

Batch fermentation for the production of L-rhamnose on the 300 l scale 300 l of main culture medium (composition as in Example 1) are sterilized in a fermenter of 450 l nominal volume. Inoculation is carried out using 4 l of a shaker flask preculture (medium from Example 1) of the strain *Pseudomonas aeruginosa* DSM 7108.

The following fermentation conditions are established: The fermentation temperature is 30° C. In the first hours of fermentation stirring is carried out at 300 rpm and from the 30th hour at 400 rpm. Up to the 10th hour of fermentation the mixture is aerated at 80 l/min, from the 10th hour of fermentation at 120 l/min and from the 30th hour of fermentation at 30 l/min. Before inoculation and after 20, 40 and 70 hours of fermentation, the trace elements from Example 1, in each case sterilized in 4 l of deionized water, are added. After a fermentation period of 112 hours, 11.3 kg of soybean oil are again added under sterile conditions. Depending on the foaming behavior, the silicone antifoamagent VP 1133 (Wacker) is metered in as required. Under said fermentation conditions, about 112 g of rhamnolipids per liter of culture solution and about 46 g/l of L-rhamnose are formed in 11 days.

The culture solution is then worked up as was described in Example 1.

We claim:

1. A process for the preparation of L-rhamnose, which comprises synthesizing rhamnolipids in a concentration of 70–120 g/l of culture solution by fermentation of *Pseudomonas aeruginosa*, wherein said *Pseudomonas aeruginosa* is selected from the group consisting of

*Pseudomonas aeruginosa* DSM 7107,

*Pseudomonas aeruginosa* DSM 7108, a mutant of *Pseudomonas aeruginosa* DSM 7107 capable of producing rhamnolipids in a concentration of 70–120 g/l of culture solution, and a mutant of *Pseudomonas aeruginosa* DSM 7108 capable of producing rhamnolipids in a concentration of 70–120 g/l of culture solution;

hydrolyzing the rhamnolipids to L-rhamnose without isolation of the rhamnolipids prior to hydrolysis; and recovering the L-rhamnose.

2. The process as claimed in claim 1, wherein the rhamnolipids are hydrolyzed to L-rhamnose in a concentration of 30–50 g/l of culture solution.

3. The process as claimed in claim 1, wherein at least one vegetable oil is added to the culture medium as a carbon source.

4. The process as claimed in claim 1, wherein the fermentation period is 4–11 days.

5. The process as claimed in claim 1, wherein said culture solution is aerated at a rate between 0.2 and 0.5 VVM.

6. The process of claim 1, wherein *Pseudomonas aeruginosa* DSM 7107 is fermented.

7. The process of claim 1, wherein *Pseudomonas aeruginosa* DSM 7108 is fermented.

8. The process of claim 3, in which the vegetable oil is soybean oil.

* * * * *